United States Patent [19]

Becker, Jr.

[11] 4,121,585

[45] Oct. 24, 1978

[54] ANTI BACKFLOW INJECTION DEVICE

[76] Inventor: Karl E. Becker, Jr., 4247 Crane Blvd., Jackson, Miss. 39216

[21] Appl. No.: 761,989

[22] Filed: Jan. 24, 1977

[51] Int. Cl.² .............................................. A61M 5/14
[52] U.S. Cl. ........................... 128/214 R; 128/DIG. 5
[58] Field of Search ............ 128/214 R, 214 D, 214.2, 128/214.4, 2.05 D, DIG. 5, 215, 2 F

[56] References Cited

U.S. PATENT DOCUMENTS

| | | | |
|---|---|---|---|
| 2,656,835 | 10/1953 | Eisenstein | 128/214 R |
| 2,955,595 | 10/1960 | Semple | 128/214 D |
| 3,332,418 | 7/1967 | Brody | 128/214 R |
| 3,861,388 | 1/1975 | Vaughn | 128/214 R |
| 4,048,995 | 9/1977 | Mittleman | 128/214 R |

FOREIGN PATENT DOCUMENTS 528,471  5/1939  United Kingdom ............. 128/DIG. 5

Primary Examiner—Dalton L. Truluck
Attorney, Agent, or Firm—Fleit & Jacobson

[57] ABSTRACT

Disclosed is an injection device for use in an IV administration set. The injection device is in the form of a Y-connector, wherein the injection port on one limb of the Y is equipped with two spaced apart piercable diaphragms. The first serves to support one or more syringes, while the second prevents the backflow of parenteral solution into the syringe.

9 Claims, 5 Drawing Figures

ANTI BACKFLOW INJECTION DEVICE

BACKGROUND OF THE INVENTION

The present invention relates to an injection device for use with intravenous administration sets. More particularly, the present invention concerns itself with an anti backflow injection device which is particularly useful for the repeated administration of intravenous drugs during surgical procedures.

In the course of the typical surgical procedure, the anesthetist delivers multiple doses of one or more intravenous anesthetics from one or more syringes, usually through the means of an IV administration set associated with the patient undergoing surgery. In this regard, the injection site of the administration set is taped to an IV pole or to the operating table itself, and when the anesthetist is ready to deliver a dose of an intravenous anesthetic drug, the needle of a syringe filled with the drug is made to puncture the rubber diaphragm of the injection port. The appropriate amount of drug is then injected directly into the flowing parenteral solution and is thereby infused into the circulatory system of the patient. The needle of the syringe is then removed, and the syringe is put aside. Then, when another dose of the same intravenous anesthetic or a dose of another drug is in order, the anesthetist repeats the above-described procedure.

One significant drawback of this procedure is the difficulty experienced by the anesthetist when attempting, with one hand, to pierce the diaphragm of the injection port with the needle of the syringe containing the intravenous drug. This seemingly simple operation is in fact quite difficult during surgery. There is no guide for directing the needle into the diaphragm. In addition, the needle cannot be left in the injection site because then there will be a certain amount of backflow of intravenous fluid into the syringe, due to the pressure head exerted by the supply of parenteral solution. This backflow dilutes the drug and renders assessment of infused drug dose very difficult. Occasionally, there is enough backflow to push the syringe plunger entirely out of the barrel of the syringe, and thus spill the drug on the floor. Accordingly, the syringe is generally removed at the end of each injection. And this, of course, increases the risk of contamination, both of the syringe needle and the contents of the syringe.

It is toward the elimination of the foregoing disadvantages, and the provision of an improved IV injection device, that the present invention is directed.

SUMMARY OF THE INVENTION

The present invention relates to an injection device which facilitates the sterile administration of an intravenous medication and the like, wherein an anesthetist or other medical personnel can perform the repeated sterile administration of intravenous drugs with just one hand.

Specifically, the inventive injection device takes the form of a Y injection site, for example, wherein the injection port on one limb of the Y is provided with two spaced apart piercable diaphragms. The first, or proximal diaphragm, serves to hold one or more syringes in place, while the second, or distal diaphragm, serves to prevent backflow of parenteral solution into the associated syringes. Therefore, when used by an anesthetist in an operating room, only one hand is needed to select the appropriate syringe for application of an anesthetic, to advance the needle of the syringe into an injection position, and to depress the plunger of the syringe to inject the appropriate amount of drug into the flowing parenteral solution. When the injection is completed, the syringe needle is conveniently and partially retracted, with one hand, so that the opening of the needle lies between the first and second diaphragms.

The section of the injection port intermediate the two diaphragms is preferably tapered from the proximal to the distal diaphragms, so that the syringe needles are guided toward the center of the distal diaphragm. Furthermore, the section intermediate the two diaphragms is of sufficient length so that most of the syringe needle resides in this section. Sterility of the needle is in this way preserved, and contamination of the syringe contents is prevented.

The arrangements of the two diaphragms and the interconnecting portion of the injection port may take many forms and shapes. Naming just a few examples, the two diaphragms may be separate elements, associated only by a rigid extension of the tubular injection port. Or, the two diaphragms may be integral with one another, with one being housed in the interior of the tubular injection port. Nor is the particular shape of the injection device critical; it may be of Y-shape, U-shape, etc. Finally, the inventive device may contain an anti backflow injection port and a conventional injection port with a single diaphragm.

It is accordingly one object of the present invention to provide an injection device for use with an IV administration set, wherein one or more syringes can remain in place during a surgical procedure, without the adverse effects of backflow of parenteral solution into the syringe.

A further object of the present invention is to provide an injection device whereby injection of an intravenous anesthetic drug and the like can be easily performed by one hand.

Another object of the present invention is to provide an injection device with which sterility of syringe needles is maximized.

A further object of the present invention is to provide an injection device having two spaced apart diaphragms in the injection port, wherein one diaphragm serves to support one or more syringes, while the other serves to prevent backflow of parenteral solution into the syringes.

Yet a further object of the present invention is to provide an injection device capable of supporting one or more syringes so that an anesthetist is easily able to perform all intravenous injections with but a single hand.

These and other objects of the present invention, as well as the attendant advantages thereof, will become more readily apparent when reference is made to the following description, taken in conjunction with the accompanying drawings.

DETAILED DESCRIPTION OF THE DRAWINGS

Figure 1:
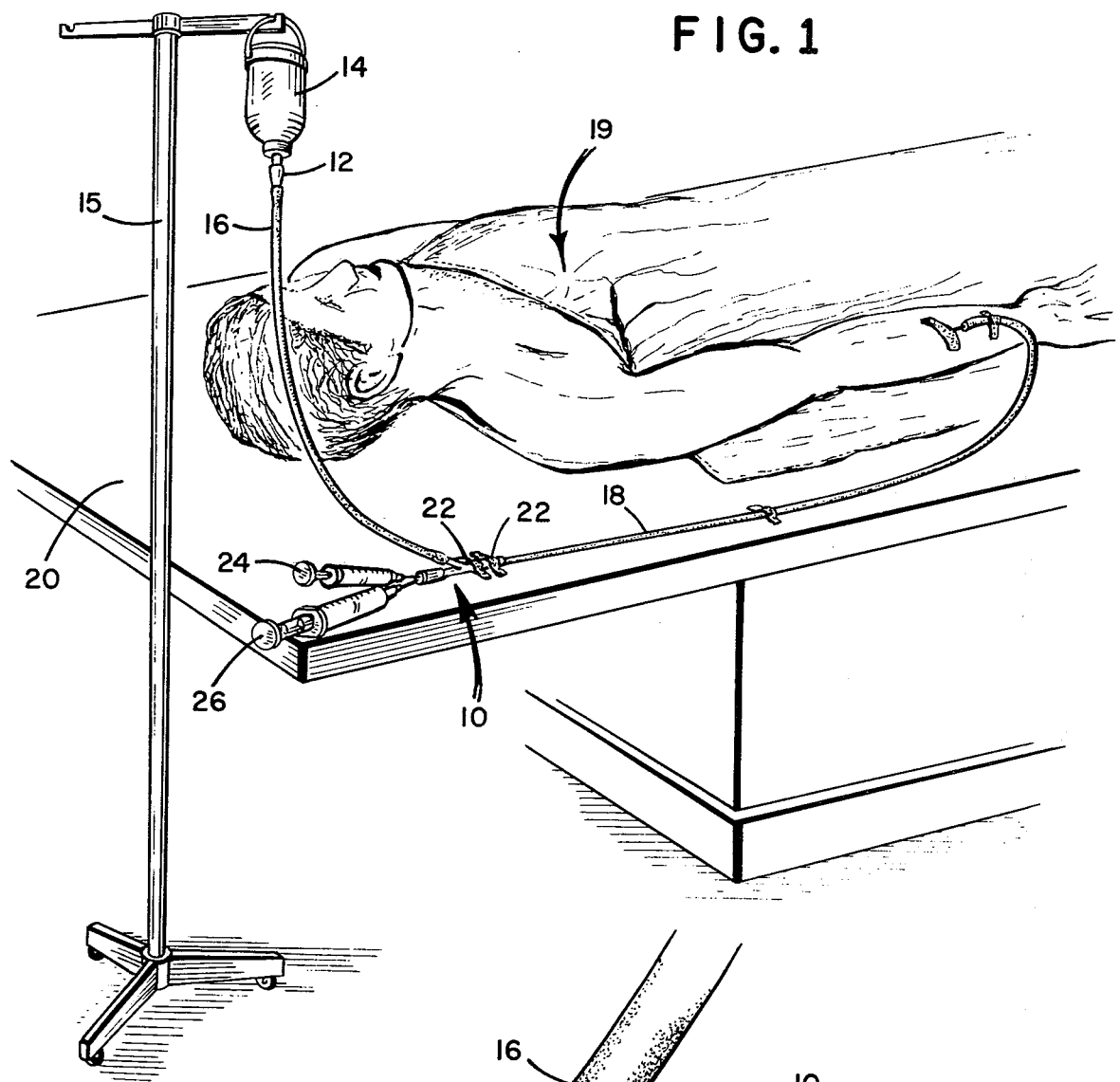
FIG. 1 is a perspective view of the inventive injection device in an operating room environment as part of an IV administration set.

With reference first to FIG. 1, the inventive injection device is shown generally at 10. The device 10 is part of an IV administration set which includes a piercer 12 for associating with a bottle (or plastic bag) 14 containing the parenteral solution being infused, and which further includes flexible tubing having a proximal portion 16 nearest bottle 14, and a distal portion 18 leading to the patient 19. The bottle 14 is shown to be suspended from a conventional IV pole 15, and the injection device 10 is shown to be taped to an operating table 20 by means of tape 22, as is common practice. Syringes 24 and 26 are shown to be inserted into and supported by the injection device 10.

Figure 2:
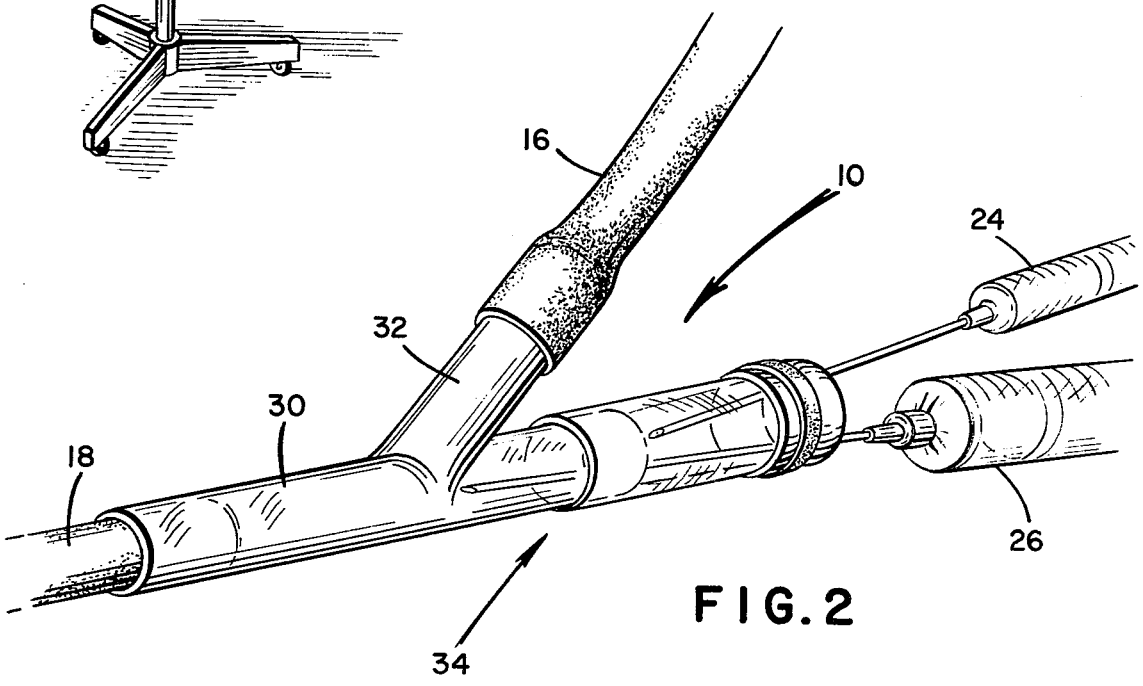
FIG. 2 is an enlarged perspective view of the inventive injection device.
Figure 3:
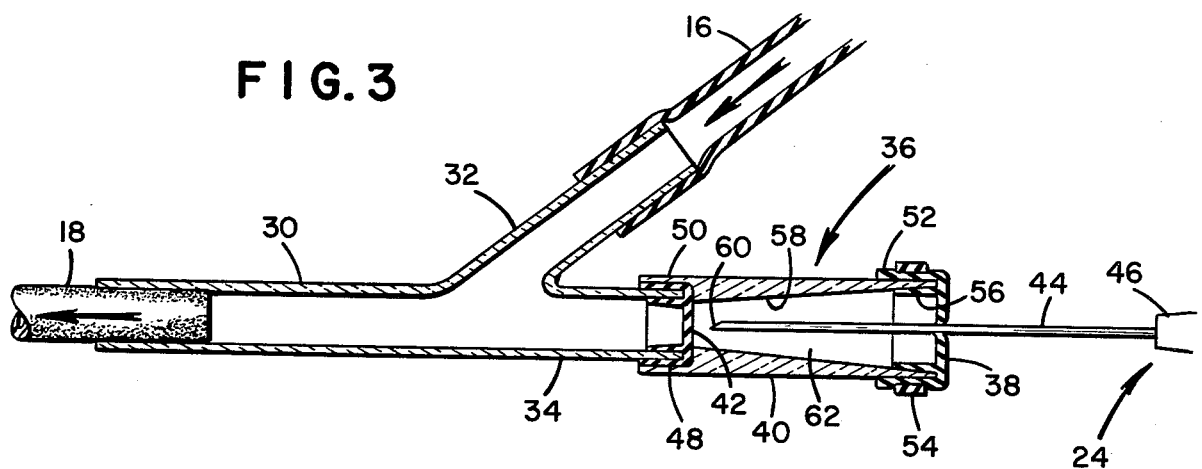
FIG. 3 is a cross-section of the inventive injection device, showing an associated syringe needle in its stand-by position.
Figure 4:
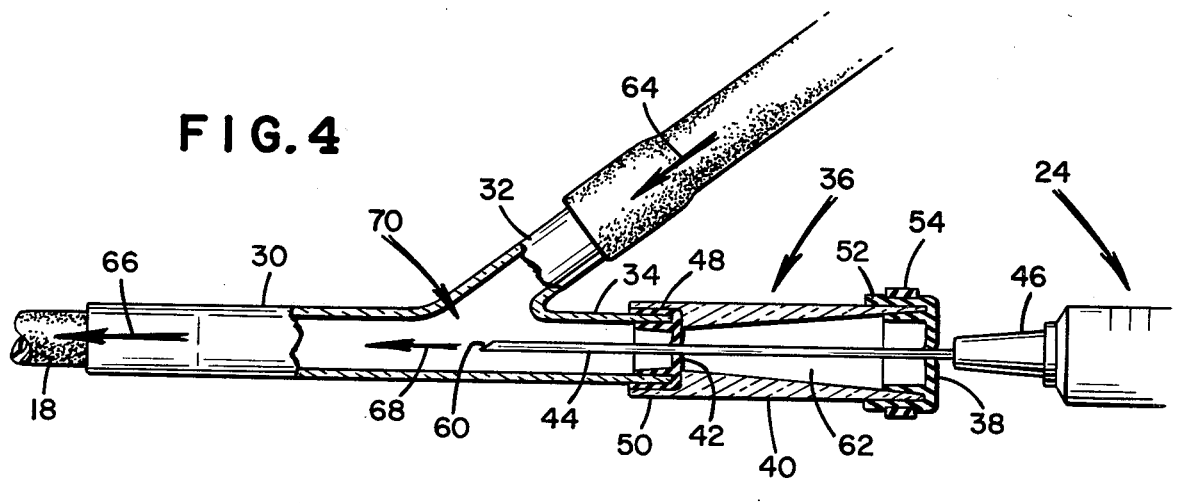
FIG. 4 is a cross-section similar to FIG. 3, showing the position of the syringe needle in its injection position.

In FIGS. 2 through 4, the details of the inventive device can better be seen. As illustrated in FIG. 2, the injection device 10 is in the form of a Y-injection site. The distal outlet portion of the injection device 10 is indicated at 30, while the proximal inlet portion is shown at 32. The injection port is represented by the number 34.

As seen best in FIG. 3, the injection port 34 is equipped with a syringe support and anti back-flow section shown generally at 36. In particular, section 36 comprises a first diaphragm 38, a guide tube 40, and a second diaphragm 42. Membranes 38 and 42 are of a material, such as rubber, which can be readily pierced by a sharp needle, and which then seals once the needle is removed. A needle is illustrated in FIG. 3 at 44, connected by its hub 46 to the associated syringe 24.

In the embodiment illustrated in FIG. 3, diaphragm 42 has a cuff 48 which is adapted to fit over the end of injection port 34. The guide tube or sleeve 40 is illustrated as having an end portion 50 which fits over the cuff 48 integral with diaphragm 42. Membrane 38 is similarly cuffed, as shown at 52, and fits over the end of tube 40 opposite from injection port 34. Diaphragm 38, with its cuff 52, is held in position by means of a rubber band 54.

It will be noted that diaphragm 38 is equipped, on its inside surface, with a protruding guide ring shown at 56. The purpose for ring 56 is to position the diaphragm 38 on the guide tube 40. Diaphragm 42 may also be provided with a guide ring. It should also be noted that the interior of guide tube 40 is inwardly tapered, as illustrated at 58, from the diaphragm 38 to the diaphragm 42.

FIG. 3 illustrates the position of the syringe needle 44 in its stand-by state. Here, the needle outlet, shown at 60, resides within a chamber 62 defined by a diaphragm 38, guide sleeve 40 and diaphragm 42. It will be noted that when in this position, diaphragm 38 serves to support and hold in place the needle 44, and hence its associated syringe. Diaphragm 42, on the other hand, serves to prevent the backflow of parenteral solution through the injection port 34 and into the syringe through needle opening 60.

With reference now to FIG. 4, when it is desired to inject from syringe 24, the syringe is advanced so that needle 44 pierces diaphragm 42. Then, the plunger on the syringe is depressed, and fluid is ejected from the opening 60 of needle 44, and combines with the flow of parenteral solution indicated by arrows 64 and 66. Arrow 68 represents the flow of fluid from syringe 24. Then, once the injection is completed, the syringe is retracted into the stand-by position illustrated in FIG. 3.

While not absolutely critical, two dimensions should be noted. The first relates to the distance between the respective diaphragms 38 and 42. Most needles used in the administration of anesthetics are one-and-one-half inches in length. Still, one-inch needles are also occasionally used. Accordingly, it is contemplated that the length of guide sleeve 40 be somewhere on the order of 1.8 centimeters. In this way, it is ensured that even a one-inch needle will be long enough to pierce both diaphragm 38 and diaphragm 42. Also, this length of the guide sleeve ensures that sterility of the portion of the needle entering the fluid path (junction 70) is preserved.

The second dimension relates to the distance between diaphragm 38 and the Y-junction, shown at 70, of the injection device 10. To maximize the passage of fluid from the syringe completely into the flowing parenteral solution, it is preferable that the distance from junction 70 to diaphragm 38 be less than 3.8 centimeters. Otherwise, there would be some possibility of fluid from the syringe being trapped in a "dead space" between junction 70 and diaphragm 42.

Figure 5:
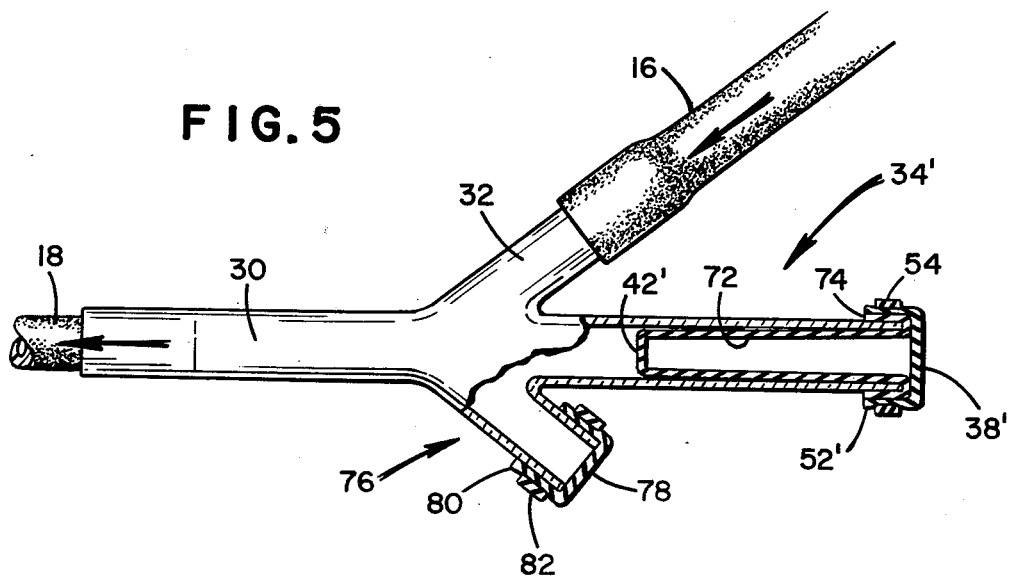
FIG. 5 is a cross-section similar to FIG. 3, showing another embodiment of the inventive injection device.

The foregoing description has concentrated on one of many possible configurations for the inventive injection device. Although many other forms are contemplated, only one additional form will be described. In this regard, it will be noted that in the embodiment shown in FIG. 3, the anti backflow section 36 is in the form of an extension appended to the base of the Y-injection site. In FIG. 5, there is illustrated another embodiment of the inventive injection device, wherein no such extension is used.

With reference then to FIG. 5, a second embodiment of the present invention will be described. Here, the Y-type injection site is similar to that shown in FIG. 3, but the injection port 34' of FIG. 5 is elongated relative to port 34 illustrated in FIG. 3. Injection port 34' is elongated to accept a diaphragm 42', integral with a sleeve 72. In this regard, the end of sleeve 72 defining diaphragm 42' is introduced to the interior of port 34', while the opposite end of sleeve 72 is folded over the end of port 34' to form an everted cuff shown at 74. Cuff 74 is then held in place by the cuff 52' of a membrane 38', with band 54, in turn, holding membrane 38' in place. A second and conventional injection port is shown at 76, equipped with a diaphragm 78, cuffed at 80, and a band at 82. Port 76 is for single injections in which the diaphragm is pierced by a needle, material injected, the needle withdrawn completely, and the syringe removed from the immediate vicinity. This port is short, so that even very short needles may be used without the potential problem of internal "dead space" or inadequate mixing of syringe contents with the parenteral intravenous infusion.

The operation of the injection device illustrated in FIG. 5 is in all respects identical to the operation of the device described above when reference was made to FIGS. 3 and 4.

Above, two specific examples of the present invention have been described. It should be appreciated, however, that many modifications of these embodiments will be readily apparent to those skilled in the art. For example, the distal diaphragm could be a disc, or could even be a one-way valve which permits the flow of a fluid from the syringe to the parenteral solution without penetration of a second diaphragm. It is accordingly the intention that the present invention not be limited by the above, but be limited only as set forth in the appended claims.

What is claimed is:

1. A device for facilitating the infusion of a drug and the like into a patient through the primary flow path of an IV administration set, the device comprising: a proximal inlet for receiving parenteral solution from a source; a distal outlet for delivering said parenteral solution to a patient; an injection site intermediate and in fluid communication with said inlet and said outlet; said proximal inlet, said distal outlet and the distal end of said injection site defining a junction region; a first piercable diaphragm at the proximal end of said injection site for supporting a syringe in a stand-by state when the needle thereof has pierced said first diaphragm; and a second piercable diaphragm spaced from said first diaphragm and at the distal end of said injection site, said second diaphragm arranged to be pierced by said needle in an injection state thereby permitting the flow of fluid from said syringe to said junction, said second diaphragm preventing the flow of parenteral solution from said junction to said syringe when said needle is in said stand-by state.

2. The device recited in claim 1, wherein the distance between said first and said second diaphragms is on the order of 1.8 centimeters.

3. The device recited in claim 1, wherein the distance from said first diaphragm to said junction is less than on the order of 3.8 centimeters.

4. The device recited in claim 1, and further comprising: a guide sleeve intermediate said first and said second diaphragms.

5. The device recited in claim 4, wherein said guide tube is inwardly tapered from said first to said second diaphragm.

6. The device recited in claim 4, wherein said second diaphragm is fit over the proximal end of an injection site; wherein the distal end of said guide sleeve is fit over said second diaphragm; and wherein said first diaphragm is mounted on the proximal end of said guide sleeve.

7. The device recited in claim 4, wherein said second diaphragm is mounted in the interior of an injection site.

8. A device for permitting at least one syringe to be left in the infusion port of an IV administration set, while preserving the sterility of the syringe needle and syringe contents, the device comprising: a proximal inlet for receiving parenteral solution from a source; a distal outlet for delivering said parenteral solution to a patient; an injection site intermediate and in fluid communication with said inlet and said outlet; said injection site for receiving said at least one syringe; said proximal inlet, said distal outlet and the distal end of said injection site defining a junction region; support means including resealable diaphragm means located at the proximal end of said injection site for receiving the needle of said at least one syringe and thereby supporting said at least one syringe in a stand-by state; and barrier means including second resealable diaphragm means spaced from said support means and at the distal end of said injection site, for being pierced by the needle of said at least one syringe thereby permitting the flow of fluid from said at least one syringe to said junction in an injection state, while maintaining a sterile field intermediate said support means and said barrier.

9. A device for facilitating the infusion of a drug, or the like, into a patient through the primary flow path of an IV administration set, the device comprising: a Y-shaped tubular means having an inlet in one arm for receiving parenteral solution from a source, an outlet in another arm for delivering said fluid to said patient, and an injection site in the third arm and being in fluid communication with said inlet and said outlet, said injection site being of a size to accept a plurality of syringes for infusing said drug; a first piercable diaphragm at the proximal end of said injection site being arranged to support said plurality of syringes in a stand-by state upon being pierced by the needles thereof; and a second piercable diaphragm spaced apart from said first diaphragm by a distance which is less than the length of the needles of said syringes and being located at the distal end of said injection site; and being arranged to be pierced by the needles of said plurality of syringes in an advanced injection state for permitting the flow of fluid from said syringes into said tubular means, said second piercable diaphragm being of a material which forms a liquid-tight seal upon withdrawal of said needles therefrom, whereby when said needles are in said stand-by state the parenteral fluid is prevented from flowing back into said syringes.

* * * * *